United States Patent [19]
Hasunuma et al.

[11] 3,944,550
[45] Mar. 16, 1976

[54] VITAMIN E OROTATE AND A METHOD OF PRODUCING THE SAME

[75] Inventors: Kyotaro Hasunuma; Masahiro Kurokawa; Takashi Abe, all of Odawara, Japan

[73] Assignee: Kanebo Ltd., Tokyo, Japan

[22] Filed: Sept. 27, 1973

[21] Appl. No.: 401,458

[30] Foreign Application Priority Data
Oct. 3, 1972  Japan.................................. 47-99270

[52] U.S. Cl. ................... 260/260; 424/69; 424/251
[51] Int. Cl.² ...................................... C07D 239/54
[58] Field of Search .................................... 260/260

[56] References Cited
UNITED STATES PATENTS
3,020,278   2/1962   Ferguson ............................. 260/260

OTHER PUBLICATIONS

Merck Index, Eighth Edition, 1968, pp. 767 and 1114–1115.

Wagner et al., *Synthetic Organic Chemistry*, 1953, John Wiley & Sons, pp. 480–482.

*Primary Examiner*—R. Gallagher
*Assistant Examiner*—Anne Marie T. Tighe
*Attorney, Agent, or Firm*—Kenyon & Kenyon

[57] ABSTRACT

Vitamin E orotate which is useful in medicines and cosmetics, is produced by esterifying vitamin E with an orotyl halide or orotic anhydride or with orotic acid in the presence of phosphorous oxychloride.

2 Claims, 1 Drawing Figure

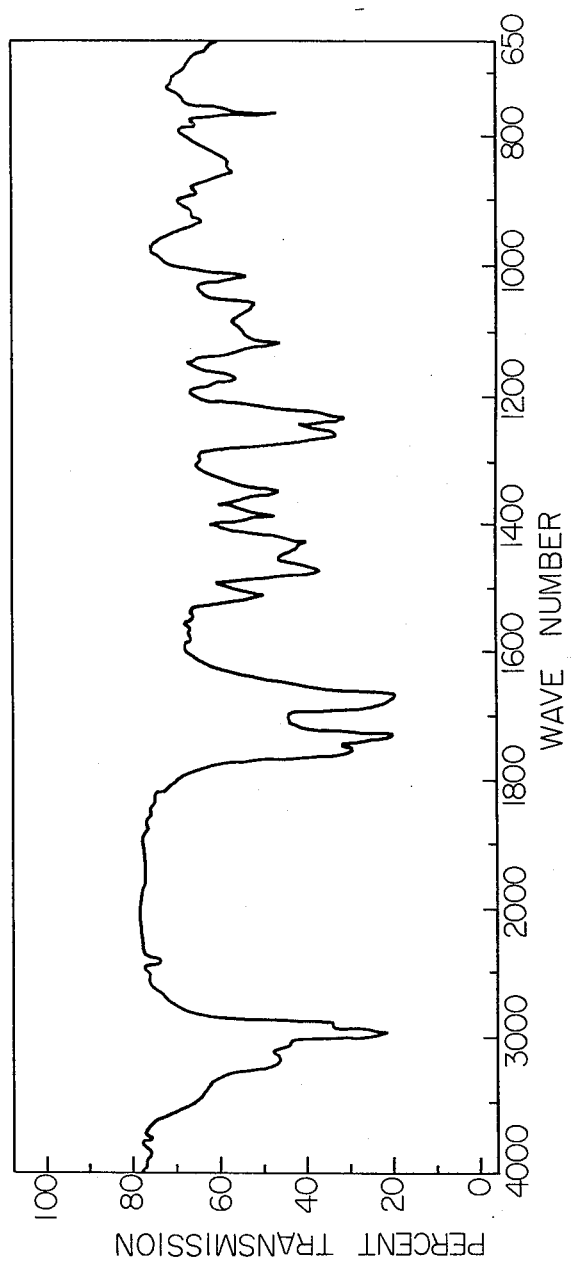

VITAMIN E OROTATE AND A METHOD OF PRODUCING THE SAME

The present invention relates to vitamin E orotate and a method of producing the same.

The term "vitamin E" used herein refers to $\alpha$-tocopherol which includes dl-$\alpha$-, d-$\alpha$-, and l-$\alpha$-tocopherols, $\beta$-tocopherol, $\gamma$-tocopherol, $\beta$-tocopherol and mixtures of two or more of the above-mentioned tocopherols. The $\alpha$-tocopherol is of the formula:

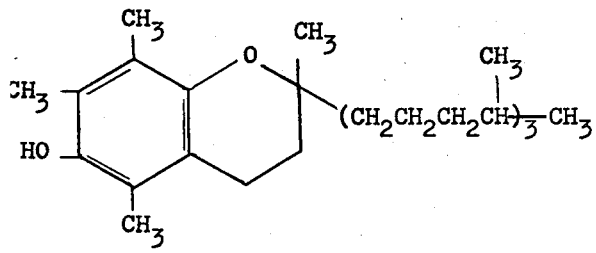

$\beta$-tocopherol and $\gamma$-tocopherol are of formulas similar to that shown above except both are without one methyl group.

It is widely known that vitamin E is effective for vasodilation of peripheral blood vessels, normalization of liver functions and muscular functions, the prevention of blood vessel sclerosis and for promoting fertility. Therefore, when ingested or applied on skin surfaces, vitamin E is very effective for curing chilblains, exudative erythema, frostbite and feeling of cold. However, vitamin E is not or only negligibly, effective for moisturizing and retarding aging of human skin.

Also, it is known that acetic ester of vitamin E tends to be easily hydrolyzed, and the hydrolyzed compound emits the unpleasant odor of acetic acid. Further, the acetic ester of vitamin E has a relatively low moisturizing effect on human skin.

Orotic acid (1,2,3,6-tetrahydro-2,6-dioxo-4-pyrimidinecarboxylic acid, uracil-6-carboxylic acid) is of the formula:

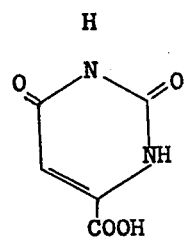

and is a pecurser of pyrimidine which is a moiety of nucleic acid and, therefore, has an influence on the metabolism of the nucleic acid. Also, it has been reported that the orotic acid is the same substance as vitamin 13 which is a factor of animal growth, or an important moiety of vitamin 13. Orotic acid may be prepared, for example, by the condensation of urea and monoethyl ester of oxalacetic acid in methyl alcohol.

It has been found that the orotic acid is effective for stimulating liver functions, promoting haematopoiesis and encouraging the growth of animals. Recently, it has also been found that orotic acid is effective for moisturizing human skin. However, orotic acid is difficult to utilize in either medicines or cosmetics, because of its negligible solubility in water and organic solvents. On the other hand, the alkali metal salts of orotic acid are soluble in water. However, when such orotic salts are utilized in cosmetics or medicines, they merely have a temporary effect, because the orotic salts cannot be maintained in organic tissue for a long period, due to its high solubility in water.

The inventors have systematically studied a wide range of orotic acid derivatives having a high solubility in water or organic solvents and methods of preparing the orotic acid derivatives. As a result of their study, the inventors have discovered that the esterification of vitamin E with orotic acid results in a relatively high yield of a novel compound, that is, vitamin E orotate having a high solubility in the conventional organic solvents. Further, it was found that the vitamin E orotate has excellent capabilities of promoting the growth of animals and of beautifying human skin. These capabilities were not expected from the properties of either orotic acid or vitamin E. It is important that the pharmaceutical and cosmetic effects of vitamin E orotate be sustained even after application or injection has ceased.

Further, vitamin E orotate is very effective for promoting the growth of human hair by stimulating the metabolism of the cells at the roots of hairs.

The objects of the present invention are to provide vitamin E orotate as a novel compound having excellent capabilities of promoting the growth of animals and beautifying human skin and hair, and methods of producing the same.

The vitamin E orotate of the present invention consists of a tocopheryl moiety and an orotyl moiety combined with the tocopheryl moiety through an ester linkage.

The vitamin E orotate of the present invention is produced by the esterification of vitamin E with orotyl halides or orotic anhydride or with orotic acid in the presence of phosphorous oxychloride.

The features of the present invention will be apparent from the following description and the accompanying drawing which shows an infra-red ray absorption spectrum of vitamin E orotate.

Vitamin E orotate of the present invention may be dl-$\alpha$-tocopherol orotate, d-$\alpha$-tocopherol orotate, l-$\alpha$-tocopherol orotate, $\beta$-tocopherol orotate, $\gamma$-tocopherol orotate, $\delta$-tocopherol orotate or mixtures of two or more of the abovementioned orotates.

Vitamin E orotate of the present invention may be prepared by the esterification of at least one tocopherol selected from $\alpha$-, $\beta$-, $\gamma$- and $\delta$-tocopherols or mixtures of two or more of the above-mentioned tocopherols, with a compound selected from orotyl halides and orotic anhydride. In this method, the orotyl halide may be selected from orotyl chloride and orotyl bromide. The above-esterification is preferably effected in an inert organic solvent selected from, for example, benzene, toluene and xylene at a temperature of, preferably, 60° to 140°C, more preferably, from 80° to 110°C. The esterification of vitamin E with the orotyl halide may be promoted in the presence of a tertiary amine, for example, pyridine or picoline, and a lewis acid, for example, aluminum chloride. Also, the esterification of vitamin E with orotic anhydride may be accelerated in the presence of a tertiary amine, for example, pyridine or picoline.

The crude vitamin E orotate mixture obtained by the above-stated esterification is filtered to remove solid impurities. The resultant filtrate is preferably neutralized by treating with a diluted alkaline aqueous solution, containing, for example, sodium carbonate or sodium bicarbonate, and washed with water. The above-stated neutralization and washing may be omitted. The filtrate is concentrated, preferably, in a non-oxidizing medium, for example, in a flow of nitrogen gas. The concentrated crude vitamin E orotate may be dissolved again in an inert solvent, for example, benzene, toluene or xylene, washed with an acid aqueous solution containing, for example, acetic acid, and with an alkaline aqueous solution as stated above, and then, concentrated once again.

The concentrated crude vitamin E orotate is purified by way of, for example, column chromatography. The purified vitamin E orotate is in the form of platy crystals.

The vitamin E orotate of the present invention may be produced by esterifying at least one tocopherol selected from $\alpha$-, $\beta$-, $\gamma$- and $\delta$-tocopherols or mixtures of two or more of the above-mentioned tocopherols, with orotic acid in the presence of phosphorous oxychloride. The esterification may be effected in an inert organic solvent selected, for instance, from benzene, toluene or xylene, at a temperature of 70° to 85°C, preferably, from 75° to 80°C. After completing the esterification, the reaction mixture is gradually poured into an aqueous solution of sodium carbonate while stirring, to neutralize phosphoric acid and hydrochloric acid produced in the reaction mixture during the esterification. The above mixture is filtered to remove the salts formed by the neutralization of the acids. The vitamin E orotate is extracted from the filtrate into an inert organic solvent, for instance, benzene, toluene or xylene and is then refined by way of, for example, column chromatography.

The vitamin E orotate of the present invention is a pale yellow platy crystal with a melting point of 183° – 188°C and is insoluble in water, but is, freely soluble in alcohols, for example, ethyl alcohol and isopropyl alcohol; aromatic hydrocarbons, for example, benzene, toluene and xylene; aliphatic hydrocarbons, for example, n-hexane; chlorinated hydrocarbons, for example, chloroform; and alicyclic hydrocarbons, for example, cyclohexane. The infra-red ray absorption spectrum of vitamin E orotate of the present invention which has been dissolved in ethyl alcohol is shown in the accompanying drawing, and the maximum absorption ($\alpha_{max}$) thereof is at 287 m$\mu$.

Vitamin E orotate of the present invention can be obtained in a relatively high yield of 70 – 80% by the methods of the present invention.

Vitamin E orotate of the present invention is useful in medicines and cosmetics. That is, vitamin E has excellent capabilities of stimulating liver functions and promoting the growth of animals. Also, vitamin E orotate is highly effective for moisturizing human skin, retarding aging of human skin and promoting growth of human hair. Therefore, vitamin E orotate is useful as an additive for cosmetics, for example, skin creams, skin lotions, face powders, skin oil, lipstick, rouges, hair cream, hair tonic, hair oil and pomade.

Various methods of practicing the present invention are illustrated by the following examples. These examples are intended merely to explain the present invention and not, in any sense, to limit the manner in which the present invention may be practiced.

EXAMPLE 1

A 1 liter three-neck flask with reflux condenser and a stirrer was charged with a mixture of 62 g of orotic acid which had been previously dried, 160 g of thionyl chloride, 600 ml of benzene and 2 ml of N,N-dimethylformamide. The flask was put in a boiling water bath and the mixture was stirred for 3 hours to chlorinate orotic acid. After completing the chlorination, the reaction mixture was filtered to separate the resultant orotyl chloride. The orotic acid chloride was washed with benzene, and dried under reduced pressure. 55.5 g of orotyl chloride was obtained.

A 1 liter three-neck flask with a stirrer and a reflux condenser was charged with a mixture of 26.3 g of orotyl chloride and 300 ml of benzene.

A 200 ml solution containing 45 g of dl-$\alpha$-tocopherol and benzene was added, by drops and while stirring, to the solution. Thereafter, the mixture was heated in a boiling water bath for 3 hours while refluxing and stirring. The reaction mixture was filtered, and the filtrate was repeatedly washed with an aqueous solution of sodium bicarbonate and water. The washed filtrate was concentrated in a flow of nitrogen gas. An oily brown product was obtained in an amount of 40 g at a yield of 70%. The oily product was refined by way of column chromatography. A pure orotic ester of dl-$\alpha$-tocopherol (vitamin E) was obtained, which was readily crystallized as platy crystals. The obtained vitamin E orotate had the following properties.

Solubility: insoluble in water, but, soluble in alcohols, such as ethyl alcohol, benzene, and chloroform.

Melting point: 183° – 188°C

Infra-red ray absorption spectrum: shown in the accompanying drawing $\lambda_{max}$ = 287 m$\mu$ (for a solution in ethyl alcohol)

$E_{1cm}^{1\%}$ = 161.3 (at 287 m$\mu$)

wherein $E_{1cm}^{1\%}$ represents an absorbance of a solution containing 1% by weight of vitamin E orotate and received in an optical cell at a thickness of 1 cm.

Elementary analysis ($C_{34}H_{52}O_5N_2$).

Calculated: H, 9.22%; C, 71.79%; N, 4.93%.

Found: H, 9.38%; C, 71.95%; N, 4.65%.

The refined vitamin E orotate was subjected to testing the growth of rats. 9 rats each weighing about 100 g were divided into three groups. They were given a mixed feed containing 70 parts by weight of barley, 0.6 part of common salt, 1.1 parts of calcium carbonate, 5.0 parts of yeast, 5.0 parts of bean oil, 9.0 parts of crude casein and 8.7 parts of fish meal. The refined vitamin E orotate was mixed with the feed in a dose of 0.01 g/kg.day for the first group, 0.1 g/kg.day for the second group and none for the third group, for a period of 3 months.

Since the weight of the rats increased with the lapse of time, weights were measured at intervals of 2 weeks, and the dose of vitamin E orotate to be mixed with the feed was increased with reference to the measured weight of rats.

The increase in weight of the rats is indicated in Table 1.

Table 1

| Group | Increase of weight (% based on the initial weight) Rearing period | | | |
|---|---|---|---|---|
| | 2 weeks | 1 month | 2 months | 3 months |
| 1 | 5 | 14 | 23 | 32 |
| 2 | 8 | 20 | 34 | 56 |
| 3 | 2 | 10 | 15 | 20 |

As Table 1 clearly indicates, the groups of rats dosed with vitamin E orotate increased in weight more than the group of rats which was not dosed. Further, it is evident that the larger the dose of vitamin E orotate, the greater the increase in the weight of the rats.

EXAMPLE 2

A mixture of 41.1 g of orotic anhydride with a melting point of 260°C and 200 ml of pyridine was charged into a 1 liter three-neck flask provided with a stirrer and a condenser, and, thereafter, 100 ml of a solution containing 44 g of dl-α-tocopherol in pyridine was gradually added by drops into the mixture. The flask containing the mixture thus prepared was put in a boiling water bath, and the mixture was heated for 3 hours while stirring and refluxing, to esterify dl-α-tocopherol with orotic anhydride. After completing the esterification, the reaction mixture was filtered, and the filtrate was repeatedly washed with an aqueous solution of sodium bicarbonate and water. The washed filtrate was concentrated in a flow of nitrogen gas. 42 g of oily brown crude product was obtained which corresponds to a yield of 75%. The crude product was refined by way of column chromatography. The oily product was converted to platy crystals. The crystalline product had the following properties:

Solubility: insoluble in water, but soluble in alcohols, for example, ethyl alcohol and cetyl alcohol, benzene and chloroform.

Melting point: 183° – 188°C
$\lambda_{max} = 287$ m$\mu$ (for an ethyl alcohol solution)
$E_{1cm}^{1\%} = 161.3$ (at 287 m$\mu$)
Elementary analysis ($C_{34}H_{52}O_5N_2$).
Calculated: H, 9.22%; C, 71.79%; N, 4.93%.
Found: H, 9.36%; C, 71.85%; N, 4.66%.

The infra-red ray absorption spectrum was the same as in the accompanying drawing.

The refined vitamin E orotate was tested for effects on moisturizing and retarding the aging of human skin.

To prepare a skin cream, 0.5 part by weight of the refined vitamin E orotate was mixed into an oil phase base consisting of 3.0 parts of bees wax, 8.0 parts of stearic acid, 3.0 parts of cetyl alcohol, 4.0 parts of anhydrous lanolin, 4.0 parts of olive oil, 5.0 parts of sorbitan monostearate, 0.1 part of p-hydroxyethyl benzoate and 0.5 part of perfume. The mixed oil phase base was emulsified in an aqueous phase base consisting of 5.0 parts by weight of propylene glycol, 3.0 parts of glycerol, 0.2 part of borax and 63.7 parts of distilled water at 80°C, and then, the resultant emulsion was gradually cooled to form a cream.

A comparative cream was prepared from the same components as mentioned above except that no vitamin E orotate was used.

In order to test the cosmetic actions of the creams prepared above, each cream was applied onto the faces of 20 women, between 25 and 45 years of age who suffered from facial wrinkles. The cream was applied twice a day, in the morning and in the evening, for 3 successive months.

Based on the results of the tests, the cosmetic actions of the cream were evaluated as illustrated in Table 2.

Table 2

| Result | Degree of effectiveness | Evaluation | |
|---|---|---|---|
| | | Cream containing vitamin E orotate | Cream containing no vitamin E orotate |
| Moisturizing effect on skin | Very effective | 18 | 0 |
| | Noticeably effective | 1 | 0 |
| | Slightly effective | 1 | 10 |
| | No effect | 0 | 10 |
| | Slightly negative effective | 0 | 0 |
| Anti-aging effect on skin | Effective for tightening skin | 18 | 1 |
| | No effect | 2 | 18 |
| | Effective for loosening skin | 0 | 1 |

In Table 2, the numerals indicate the number of women evaluating the respective creams as having the described degree of effectiveness of the result As Table 2 definitely illustrates, vitamin E orotate contained in the cream is very effective for moisturizing the face and preventing the skin from aging.

EXAMPLE 3

A three-neck flask provided with a thermometer, a condenser and a stirrer was charged with 300 ml of benzene, 5.8 g of phosphorous oxychloride. 15.6 g of orotic acid which had been dried, and 43.1 g of dl-α-tocopherol. The mixture in the flask was heated at a temperature of 75° to 80°C for 3 hours while stirring to directly esterify dl-α-tocopherol with orotic acid. AFter completing the esterification, the reaction mixture was gradually poured into 100 ml of an aqueous solution containing 12.0 g of sodium carbonate while stirring, and the mixture was filtered.

The filtrate was received in a separating funnel to isolate the benzene solution phase from the aqueous solution phase. The benzene solution thus separated was repeatedly washed with the sodium carbonate solution and water. The washed benzene solution was concentrated in a flow of nitrogen gas. 41 g of an oily brown crude product was obtained, representing a yield of 73%. The crude product was purified by way of column chromatography. The pure product was a platy crystalline substance and had the same properties as those in Example 1.

Elementary analysis ($C_{34}H_{52}O_5N_2$).
Calculated: H, 9.22%; C, 71.79%; N, 4.93%.
Found: H, 9.37%; C, 71.85%; N, 4.75%.

The infra-red ray absorption spectrum of the product was the same as in the accompanying drawing.

What we claim is:

1. Vitamin E orotate consisting of a tocopheryl moiety selected from α-, β-, γ- and δ-tocopheryl groups and an unsubstituted orotyl moiety combined with said tocopheryl moiety through an ester linkage.

2. Vitamin E orotate as claimed in claim 1, wherein said α-tocopheryl group is selected from dl-α-, d-α- and l-α-tocopheryl groups.

* * * * *